United States Patent
Pecquois

(10) Patent No.: US 11,876,352 B2
(45) Date of Patent: Jan. 16, 2024

(54) PULSED ELECTRIC DISCHARGE DEVICE

(71) Applicant: ADM28 FRANCE, Toulouse (FR)

(72) Inventor: Romain Pecquois, Villeneuve-Tolosane (FR)

(73) Assignee: ADM28 FRANCE, Toulouse (FR)

(*) Notice: Subject to any disclaimer, the term of this patent is extended or adjusted under 35 U.S.C. 154(b) by 379 days.

(21) Appl. No.: 17/311,265

(22) PCT Filed: Dec. 17, 2019

(86) PCT No.: PCT/EP2019/085609
§ 371 (c)(1),
(2) Date: Jun. 4, 2021

(87) PCT Pub. No.: WO2020/141068
PCT Pub. Date: Jul. 9, 2020

(65) Prior Publication Data
US 2022/0021190 A1  Jan. 20, 2022

(30) Foreign Application Priority Data

Dec. 31, 2018 (FR) .................................. 1874395

(51) Int. Cl.
*H03K 3/00* (2006.01)
*H01T 15/00* (2006.01)
(Continued)

(52) U.S. Cl.
CPC ............. *H01T 15/00* (2013.01); *B21D 26/12* (2013.01); *G01R 19/0084* (2013.01);
(Continued)

(58) Field of Classification Search
CPC .... H01T 15/00; B21D 26/12; G01R 19/0084; H03K 3/53; H03K 3/357; A61B 17/22022; G01V 1/17; G10K 15/06
See application file for complete search history.

(56) References Cited

U.S. PATENT DOCUMENTS

2003/0006721 A1* 1/2003 Kinbara ............... H03K 3/53
                                                        315/363
2005/0113722 A1  5/2005 Schultheiss
(Continued)

FOREIGN PATENT DOCUMENTS

EP          2274741 A2     1/2011
WO    WO 2010/146016 A1   12/2010

OTHER PUBLICATIONS

Search Report from the French Intellectual Property Office on corresponding FR application (FR1874395) dated Sep. 6, 2019.
(Continued)

*Primary Examiner* — Tuan T Lam
(74) *Attorney, Agent, or Firm* — KOS IP Law LLP

(57) ABSTRACT

The present invention concerns a device for pulsed electric discharge in a liquid comprising a control module configured to control a voltage generator such that the voltage generator applies a predetermined heating voltage setpoint between electrodes during a heating period until a pulsed electric discharge is obtained between the electrodes, in order to measure the breakdown voltage during the pulsed electric discharge, in order to estimate the quantity of energy supplied to the liquid during the heating period, referred to as the "quantity of heating energy", from the predetermined heating voltage setpoint and the measured breakdown voltage, and in order to determine a new heating voltage setpoint to apply between the electrodes of the at least one pair of electrodes at the next pulsed electric discharge based on the estimated quantity of heating energy and a predefined breakdown voltage setpoint.

10 Claims, 1 Drawing Sheet

(51) Int. Cl.
*B21D 26/12* (2006.01)
*G01R 19/00* (2006.01)
*E21B 43/24* (2006.01)
*H03K 3/537* (2006.01)
*H03K 3/53* (2006.01)

(52) U.S. Cl.
CPC ............ *E21B 43/2401* (2013.01); *H03K 3/53* (2013.01); *H03K 3/537* (2013.01)

(56) References Cited

U.S. PATENT DOCUMENTS

| | | | |
|---|---|---|---|
| 2010/0294743 A1* | 11/2010 | Hashimoto | B23H 1/022 |
| | | | 219/121.34 |
| 2012/0157892 A1 | 6/2012 | Reitmajer et al. | |
| 2014/0074111 A1 | 3/2014 | Hakala et al. | |
| 2021/0268471 A1* | 9/2021 | Dosta | H05B 1/0297 |
| 2022/0234899 A1* | 7/2022 | Medvedev | C25B 9/00 |

OTHER PUBLICATIONS

International Search Report and Written Opinion on corresponding PCT application (PCT/EP2019/085609) from International Searching Authority (EPO) dated Mar. 10, 2020.

* cited by examiner

PULSED ELECTRIC DISCHARGE DEVICE

TECHNICAL FIELD

The present invention relates to the field of power electronics and is more particularly concerned with a device and method for pulsed electric discharge in a liquid. Such a method and device find application especially in electrohydraulic forming, seismic tools, oil well stimulation or lithotripsy.

BACKGROUND

In power electronics, it is known to use a pulsed electric discharge device allowing a very high intensity current under very high voltage between two electrodes immersed in a liquid to be transferred in a fraction of a second. The voltage between both electrodes is supplied by an external power supply, for example between 1 and 40 kV, comprising capacitive modules allowing electric energy to be stored and restored in a fraction of a second in the form of a very high intensity current under very high voltage.

In a known way, during a high voltage pulsed electric discharge in a liquid, for example in water, two phases can be distinguished: a first so-called "heating" or "pre-discharge" phase, followed by a second so-called "breakdown" phase. The heating phase is triggered by switching on one of the electrodes at a first high voltage value, for example 20 kV, the other electrode being connected to a ground setting the potential reference, for example to 0 kV. During the heating phase, the voltage defined between both electrodes allows the liquid to be heated to boiling point in order to create a gas channel to create breakdown conditions. The supply of energy to the liquid causes a voltage drop across the electrodes until a second voltage value is reached at which the energy supplied to the liquid is sufficiently high to trigger breakdown. The breakdown corresponds to an electric discharge propagating in the gas channel and creating an electric arc allowing the current to flow between both electrodes.

However, this type of device has several drawbacks, especially in its application to electrohydraulic forming of a metal part. First of all, the voltage level at the time of arc creation is not controlled. The energy concentrated between the electrodes, which is then converted into a pressure wave, is therefore not constant from one shot to another. In its application to forming, this results in that, from one test to another, the forming pressure applied to the part is not identical. But such differences in forming pressure can turn out to be too great, so that some of the parts produced are not compliant.

DETAILED DESCRIPTION

Figure 1:
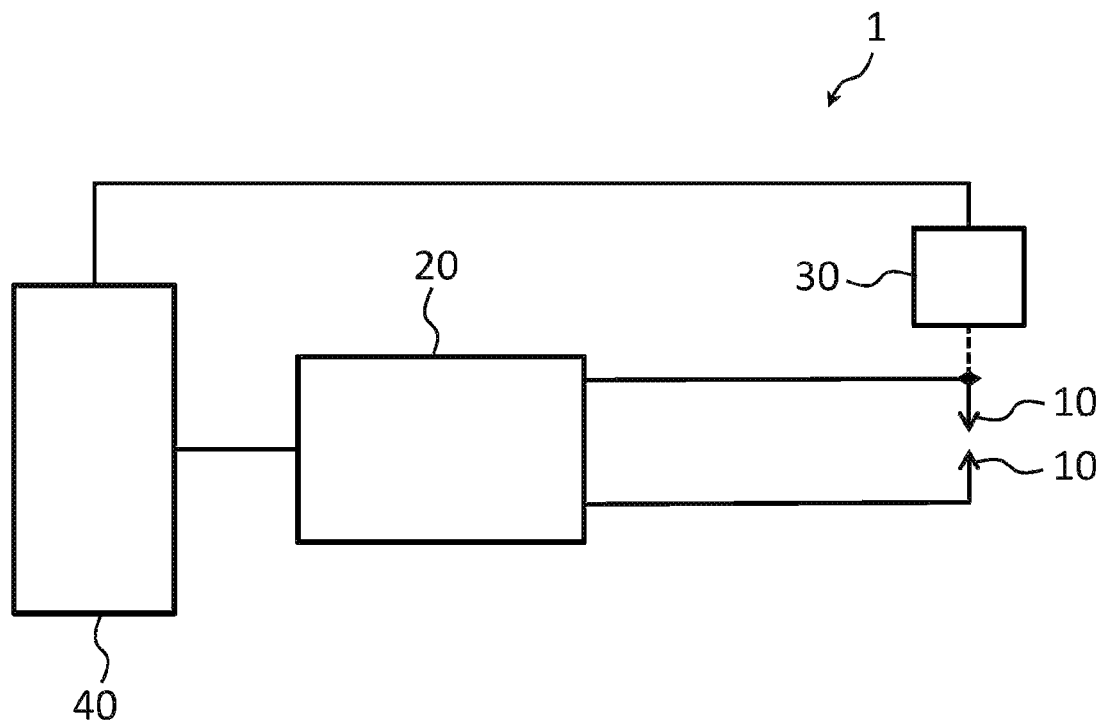
FIG. 1 schematically illustrates one embodiment of the pulsed electric discharge device according to the invention.

The purpose of the present invention is to at least partly remedy these drawbacks by providing a simple, reliable and effective solution for a pulsed electric discharge device.

To this end, the invention firstly has as its object a device for pulsed electric discharge in a liquid, said device comprising at least one pair of electrodes, configured to be immersed in said liquid, and a voltage generator, capable of applying a heating voltage between the electrodes of said at least one pair of electrodes for a so-called "heating" period in order to heat the liquid until a pulsed electric discharge is caused in said liquid, said device being remarkable in that it further comprises a control module configured to:
- control the voltage generator from a predetermined heating voltage set point so that said voltage generator applies a heating voltage between the electrodes of said at least one pair of electrodes during the heating period until a pulsed electric discharge is obtained between said electrodes,
- measure the voltage across the electrodes to determine the breakdown voltage at which the pulsed electric discharge occurred,
- estimate the quantity of energy supplied to the liquid during the heating period, the so-called "quantity of heating energy", from the predetermined heating voltage set point and the measured breakdown voltage,
- determine a new heating voltage set point to be applied between the electrodes of said at least one pair of electrodes at the next pulsed electric discharge from the quantity of heating energy estimated and a predefined breakdown voltage set point.

The device according to the invention makes it possible to apply a heating voltage set point that is a function of both the quantity of energy dissipated during the previous pulsed electric discharge and the energy losses generated during the heating period of the previous shot, said losses being proportional to the breakdown voltage. Such a set point allows the voltage level to be accurately controlled at the time of shot. The energy concentrated between the electrodes, which is then converted into a pressure wave, is thus substantially constant from one shot to another. In its application to forming, this results in that, from one test to the next, the forming pressure applied to the part is substantially the same, thus making the parts compliant.

According to one aspect of the invention, the device is configured to determine the new heating voltage set point by calculating the median or mean of the quantities of heating energy previously estimated by the device during the previous shot or shots.

The new heating voltage set point can be determined from the median or mean of the quantities of heating energy previously estimated at the last N iterations, N being a preferably odd, natural integer, and for example greater than or equal to 3.

The breakdown voltage set point can be adjusted from one shot to another, for example manually by an operator or automatically as a function of a target value to be reached over the course of the shots.

According to one characteristic of the invention, the device comprises a measurement module such as, for example, a probe or a sensor, configured to measure the breakdown voltage across the electrodes.

Advantageously, the control module is configured to calculate the quantity of heating energy from the breakdown voltage measured at the last shot and the heating voltage set point applied at the last shot according to the following formula:

$$E_{loss} = \tfrac{1}{2} \times C \times (V_C^2 - V_B^2)$$

where $E_{loss}$, is the quantity of heating energy, C corresponds to the capacitance of the voltage generator, $V_C$ is the heating voltage set point applied at the last shot and $V_B$ is the breakdown voltage measured at the last shot.

According to one aspect of the invention, the control module is configured to determine the new heating voltage set point to be applied between the electrodes at the next shot from the value of the quantity of heating energy estimated at the last shot, or the median calculated if necessary, and the predefined breakdown voltage set point, for example manually by an operator or automatically so as to reach a target value, according to the following formula:

$$V_C = \sqrt{\left(\frac{2E_{loss}}{C} + V_{B\_CONS}^2\right)}$$

where $V_C$ is the new heating voltage set point calculated, $E_{loss}$ is the quantity of heating energy value determined in the last shot and $V_{B\_CONS}$ is the target breakdown voltage set point.

Preferably, the heating period is between 5 µs and 500 ms.

Even more preferably, the breakdown voltage is between 1 and 40 kV.

According to one characteristic of the invention, subsequently to starting up the device, the initial value of the heating voltage set point is determined from a predetermined quantity of heating energy and a predetermined breakdown voltage value, which are for example stored in a memory zone of the device.

In one exemplary embodiment, the voltage generator comprises a capacitive module, connected to one of the electrodes of the at least one electrode pair, comprising for example one or more capacitors.

The invention also relates to a method for generating an electric discharge in a liquid from a pulsed electric discharge device as set forth above, said method, implemented by the control module, being remarkable in that it comprises the steps of:

controlling the voltage generator from a predetermined heating voltage set point so that said voltage generator applies a heating voltage between the electrodes of said at least one pair of electrodes until a pulsed electric discharge is obtained between said electrodes measuring the voltage across the electrodes to determine the so-called "breakdown" voltage at which the pulsed electric discharge occurred, estimating the quantity of energy supplied to the liquid during the heating period, the so-called "quantity of heating energy", from the predetermined heating voltage set point and the breakdown voltage measured, determining a new heating voltage set point to be applied between the electrodes of said at least one pair of electrodes at the next pulsed electric discharge from the quantity of heating energy estimated and a predefined breakdown voltage set point.

According to one aspect of the invention, the method is repeated a plurality of times and the new heating voltage set point is determined at each iteration from the quantity of heating energy estimated at the previous iteration or the quantities of heating energy estimated at the previous iterations.

Preferably, the new heating voltage set point is determined from the median or mean of the quantities of heating energy previously estimated at the previous iterations.

The new heating voltage set point can be determined from the median or mean of the quantities of heating energy previously estimated at the last N iterations, N being a natural integer, for example greater than or equal to 3.

Preferably, subsequently to starting up the device, the method is first repeated at least ten times in order to calibrate the device to allow subsequent shots at accurate set points, especially allowing a target breakdown voltage value to be reached.

Advantageously, the quantity of heating energy is determined from the breakdown voltage measured at the last shot and the predetermined heating voltage set point applied at the last shot according to the following formula:

$$E_{loss} = \tfrac{1}{2} \times C \times (V_C^2 - V_B^2)$$

where $E_{loss}$ is the quantity of heating energy, C corresponds to the capacitance of the voltage generator, $V_C$ is the set point heating voltage applied at the last shot and $V_B$ is the breakdown voltage measured at the last shot.

According to one aspect of the invention, the new heating voltage set point to be applied between the electrodes in the next shot is calculated from the heating energy quantity value estimated, or the median calculated if applicable, and the predefined breakdown voltage set point, for example manually by an operator or automatically so as to achieve a target value, according to the following formula:

$$V_C = \sqrt{\left(\frac{2E_{loss}}{C} + V_{B\_CONS}^2\right)}$$

where $V_C$ is the new calculated heating voltage set point, $E_{loss}$ is the heating energy quantity value determined in the last shot and $V_{B\_CONS}$ is the target breakdown voltage set point.

Further characteristics and advantages of the invention will become apparent from the following description made with reference to the appended figures given as non-limiting examples and in which identical references are given to similar objects.

FIG. 1 schematically illustrates one embodiment of the pulsed electric discharge device according to the invention.

Figure 2:
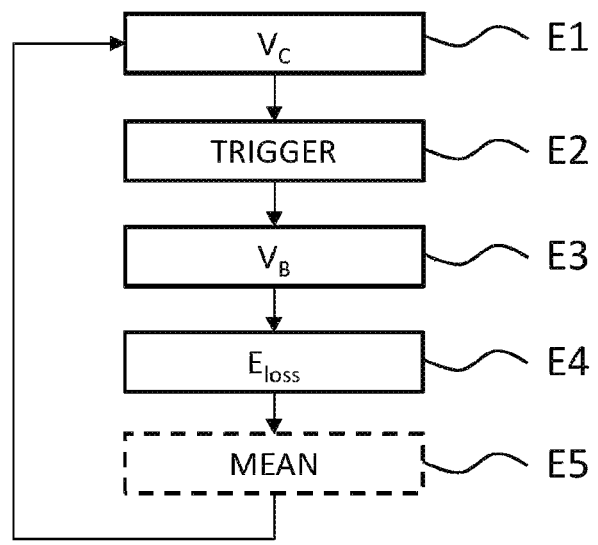
FIG. 2 schematically illustrates one embodiment of the method according to the invention.

FIG. 2 schematically illustrates one embodiment of the method according to the invention.

The device according to the invention enables pulsed electric discharges to be performed in a liquid, for example water or blood. The device according to the invention can especially be used to perform electrohydraulic forming of metal parts, to perform geophysical prospecting by generating seismic waves, to improve production of oil wells (stimulation) or to treat kidney stones by lithotripsy.

One embodiment of the device 1 according to the invention has been represented in FIG. 1. In this embodiment, the device 1 comprises a single pair of electrodes 10, a voltage generator 20, a measurement module 30 and a control module 40. It will be noted that in another embodiment, the device 1 could comprise more than one pair of electrodes 10.

The pair of electrodes 10 is configured to be immersed in the liquid in which a series of pulsed electric discharges are to be performed. More specifically, the pair of electrodes 10 is configured to receive a voltage applied between both electrodes 10 by the voltage generator 20 for a so-called "heating" period to heat the liquid until a pulsed electric discharge is generated causing an electric arc between both electrodes 10. The voltage at which the pulsed electric discharge occurs is called the "breakdown voltage". The electrode 10 that is connected to the positive terminal of the voltage generator 20 is referred to as the "charging" electrode, while the electrode 10 that is connected to the negative terminal of the voltage generator 20 is referred to as the "receiving" electrode.

During a shot, electric charges propagate from the charging electrode 10 to the receiving electrode 10 in the volume of liquid and gas separating them. The electrodes 10 may, for example, be generally hollow cylindrical, rotationally symmetric in shape. Preferably, the electrodes 10 are aligned "end to end", that is, arranged so that their respective longitudinal axes (not represented) coincide and have free ends spaced apart by a predetermined fixed distance, for example, between about 1 and 50 mm, preferentially between 1 and 25 mm (increasing the distance between the electrodes 10 increases the energy deposited between said electrodes 10), and facing each other along the axial direction (direction of the axes of symmetry). During a pulsed electric discharge, the electric arc occurs between these free ends, whose facing annular end faces are substantially planar (in transverse planes).

The voltage generator 20 is configured to apply a heating voltage between the electrodes 10 from a predetermined heating voltage set point Vo provided by the control module 40 until a pulsed electric discharge is triggered in the liquid. The period during which the heating voltage Vo is applied between the electrodes 10 is referred to as the "heating period".

The voltage generator 20 may be in the form of a plurality of capacitors or a constant current voltage generator. The use of a plurality of capacitors allows a voltage in the order of a few kilovolts to be provided in a very short time, for example in the order of 10 ms.

The measurement module 30 enables the breakdown voltage at which the pulsed electric discharge occurs during a shot to be measured. The measurement module 30 may, for example, be in the form of a probe or a voltage measurement sensor.

The control module 40 is configured to control the voltage generator 20 from a predetermined heating voltage set point so that said voltage generator 20 applies the voltage corresponding to this set point between the electrodes 10 during the heating period in order to cause a pulsed electric discharge between said electrodes 10. More specifically, the control module 40 is configured to send a heating voltage set point to the voltage generator 20 so that upon receiving said set point, the voltage generator 20 applies the voltage value corresponding to that set point across the electrodes 10 in order to trigger a pulsed electric discharge across said electrodes. Preferably, the heating period is between 5 μs and 500 ms and the discharge voltage is between 1 and 40 kV.

The control module 40 is configured to collect voltage measurements made by the measurement module 30 and estimate the quantity of energy supplied to the liquid during the heating period, referred to as the "quantity of heating energy" $E_{loss}$ from the predetermined heating voltage set point $V_C$ applied at the last shot and the breakdown voltage value $V_B$ measured at the last shot.

The control module 40 is configured to determine a new heating voltage set point $V_C$ to be applied between the electrodes 10 in order to perform the next pulsed electric discharge.

The control module 40 is configured to measure the voltage across the electrodes to determine the breakdown voltage $V_B$, at which the pulsed electric discharge occurs during a shot.

The control module 40 is configured to calculate the quantity of heating energy $E_{loss}$ from the measured breakdown voltage $V_B$ and the predetermined heating voltage set point $V_C$, applied in the last shot it controlled via the voltage generator 20, according to the following formula:

$$E_{loss} = \tfrac{1}{2} \times C \times (V_C^2 - V_B^2)$$

where C is the capacitance value of the capacitors of the voltage generator 20.

At start of the device 1, the heating voltage set point is determined from a predetermined initial quantity of heating energy $E_{loss}$ and a predefined breakdown voltage set point $V_{B\_CONS}$ allowing a pulsed electric discharge between the electrodes 10. Once at least one shot has been performed, the new heating voltage set point is determined from the last heating energy quantity or quantities $E_{loss}$ calculated by said control module 40.

Preferably, the device is configured to determine the new heating voltage set point $V_C$ by calculating the median or mean of quantities of heating energy $E_{loss}$ previously estimated. The new heating voltage set point can be determined from the median or mean of the quantities of heating energy $E_{loss}$ previously estimated at the last N iterations, N being a preferably odd, natural integer, and for example greater than or equal to 3. Preferably, the control module 40 is configured to recalculate the median or mean of the quantities of heating energy $E_{loss}$ after each pulsed electric discharge.

The control module 40 may, for example, comprise a calculator, processor, or microcontroller to perform the different aforementioned tasks.

One exemplary implementation of the device 1 will now be described with reference to FIG. 2.

The control module 40 first calculates, in a step E1, a heating voltage set point $V_C$ value to be applied to trigger the next shot from a heating energy quantity $E_{loss}$ value, and a breakdown voltage $V_B$ value according to the following formula:

$$E_{loss} = \tfrac{1}{2} \times C \times (V_C^2 - V_B^2)$$

At start of the device 1, the initial predetermined quantity of heating energy $E_{loss}$ value and the initial set point voltage $V_{B\_CONS}$ value are stored in a memory zone of the control module 40 or entered manually by an operator.

The heating voltage set point $V_C$ is calculated by the control module 40 according to the following formula:

$$V_C = \sqrt{\left(\frac{2E_{loss}}{C} + V_{B\_CONS}^2\right)}$$

The control module 40 then controls the voltage generator 20 so that said voltage generator 20 applies, in a step E2, the heating voltage set point $V_C$, determined in step E1, between the electrodes 10 until a pulsed electric discharge is obtained between said electrodes 10 (TRIGGER).

During this shot, the measurement module 30 measures, in a step E3, the breakdown voltage $V_B$ across the electrodes 10 and sends this measurement to the control module 40.

The control module 40 then calculates, in a step E4, an estimate of the quantity of heating energy $E_{loss}$ used during the last shot from the breakdown voltage $V_B$ measured in step E3 and the heating voltage set point $V_C$ used in step E2 according to the following formula:

$$E_{loss} = \tfrac{1}{2} \times C \times (V_C^2 - V_B^2)$$

where $V_C$ is the heating voltage set point and $V_B$ is the breakdown voltage value measured in step E3.

Preferably, the control module 40 then calculates in an optional step E5 the median MEAN of the quantities of heating energy $E_{loss}$ estimated from previous shots, if available.

The control module 40 then determines a new heating voltage set point $V_C$ to be applied between the electrodes 10 at the next shot by repeating step E1 from the quantity of heating energy $E_{loss}$ value estimated, or from the median MEAN calculated if necessary, and from the predefined breakdown voltage set point $V_B$, for example manually by an operator or automatically so as to reach a target breakdown voltage value between the electrodes from one shot to the next, according to the following formula:

$$V_C = \sqrt{\left(\frac{2E_{loss}}{C} + V_{B\_CONS}^2\right)}$$

where $E_{loss}$ is the quantity of heating energy value determined in step E4 and $V_B$ is the target breakdown voltage set point.

The control module 40 repeats steps E1 through E4 (or E5) in order to perform a series of pulsed electric discharges with substantially constant energy.

Subsequently to starting up the device 1, the method can be carried out several times in order to calibrate the device 1 and obtain accurate heating voltage set points $V_C$ for subsequent shots, which can then be used in production, for example for electrohydraulic forming.

The invention thus advantageously makes it possible to define accurate and refined heating voltage set points in order to allow regularity of shots in terms of breakdown voltage. It is to be noted that the present invention is not limited to the examples described above and is susceptible to numerous alternatives accessible to the person skilled in the art.

The invention claimed is:

1. A device for pulsed electric discharge in a liquid, said device comprising at least a pair of electrodes, configured to be immersed in said liquid, and a voltage generator capable of applying a heating voltage between the electrodes of said at least one pair of electrodes for a so-called "heating" period in order to heat the liquid until a pulsed electric discharge is caused in said liquid, said device being characterized in that it further comprises a control module configured to:
   control the voltage generator from a predetermined heating voltage set point so that said voltage generator applies a heating voltage between the electrodes of said at least one pair of electrodes during the heating period until a pulsed electric discharge is obtained between said electrodes,
   measure the voltage across the electrodes in order to determine the breakdown voltage at which the pulsed electric discharge occurred,
   estimate the quantity of energy supplied to the liquid during the heating period, so-called "quantity of heating energy", from the predetermined heating voltage set point and the breakdown voltage measured,
   determine a new heating voltage set point to be applied between the electrodes of said at least one pair of electrodes at the next pulsed electric discharge from the heating energy quantity estimated and a predefined breakdown voltage set point.

2. The device according to claim 1, said device being configured to determine the new heating voltage set point by calculating the median or mean of the quantities of heating energy previously estimated by the device during the previous shot(s).

3. The device according to claim 2, wherein the new heating voltage set point is determined from the median of the quantities of heating energy previously estimated at the last N iterations, N being an odd natural number greater than or equal to 3.

4. The device according to claim 1, comprising a measurement module configured to measure the breakdown voltage across the electrodes.

5. The device according to claim 1, wherein the control module is configured to calculate the quantity of heating energy from the breakdown voltage measured at the last shot and the heating voltage set point applied at the last shot according to the formula:

$$E_{loss} = \frac{1}{2} \times C \times (V_C^2 - V_B^2)$$

where $E_{loss}$ is the quantity of heating energy, C corresponds to the capacitance of the voltage generator, $V_C$ is the heating voltage set point applied at the last shot and $V_B$ is the breakdown voltage measured.

6. The device according to claim 1, wherein the control module is configured to determine the new heating voltage set point to be applied between the electrodes in the next shot from the value of the quantity of heating energy estimated in the last shot, or from the median calculated if necessary, and from the predefined breakdown voltage set point, according to the following formula:

$$V_C = \sqrt{\left(\frac{2E_{loss}}{C} + V_{B\_CONS}^2\right)}$$

7. A method for generating an electric discharge in a liquid from a pulsed electric discharge device according to claim 1, said method, implemented by the control module, being characterized in that it comprises the steps of:
   controlling the voltage generator from a predetermined heating voltage set point so that said voltage generator applies a predetermined heating voltage set point between the electrodes of said at least one pair of electrodes until a pulsed electric discharge is obtained between said electrodes,
   measuring the voltage across the electrodes in order to determine the so-called "breakdown" voltage at which the pulsed electric discharge occurred,
   estimating the quantity of energy supplied to the liquid during the heating period, the so-called "quantity of heating energy", from the predetermined heating voltage set point and the breakdown voltage measured,
   determining a new heating voltage set point to be applied between the electrodes of said at least one pair of electrodes at the next pulsed electric discharge from the quantity of heating energy estimated and a predefined breakdown voltage set point.

8. The method according to claim 7, wherein, with said method being repeated a plurality of times, the new heating voltage set point is determined at each iteration from the quantity(ies) of heating energy estimated at the previous iteration or iterations.

9. The method according to claim 7, wherein the new heating voltage set point is determined from the median of the quantities of heating energy previously estimated at the previous iterations.

10. The method according to claim 7, wherein the quantity of heating energy is determined from the predetermined heating voltage set point applied at the last shot and the breakdown voltage measured at the last shot according to the following formula:

$$E_{loss} = \tfrac{1}{2} \times C \times (V_C^2 - V_B^2)$$

where C corresponds to the capacitance of the voltage generator.

* * * * *